(12) United States Patent
Wotton

(10) Patent No.: US 11,278,162 B1
(45) Date of Patent: Mar. 22, 2022

(54) PERSONAL BODY CLEANING AND STOOL COLLECTION DEVICE AND METHOD

(71) Applicant: Douglas William Wotton, Kent, WA (US)

(72) Inventor: Douglas William Wotton, Kent, WA (US)

( * ) Notice: Subject to any disclaimer, the term of this patent is extended or adjusted under 35 U.S.C. 154(b) by 91 days.

(21) Appl. No.: 16/595,376

(22) Filed: Oct. 7, 2019

Related U.S. Application Data

(60) Provisional application No. 62/742,915, filed on Oct. 8, 2018.

(51) Int. Cl.
| | | |
|---|---|---|
| *A47K 7/08* | (2006.01) | |
| *A61B 10/00* | (2006.01) | |
| *A47K 17/00* | (2006.01) | |

(52) U.S. Cl.
CPC ............ *A47K 7/08* (2013.01); *A61B 10/0038* (2013.01); *A47K 2017/006* (2013.01)

(58) Field of Classification Search
CPC . A47K 7/028; A47K 7/06; A47K 7/08; A61G 9/00; A61G 9/003; A61G 9/006; A61G 9/02; A61B 10/0038; A61F 5/449; A61F 5/451
See application file for complete search history.

(56) References Cited

U.S. PATENT DOCUMENTS

| | | | | | |
|---|---|---|---|---|---|
| 4,067,335 | A | * | 1/1978 | Silvanov | A61F 5/455 604/328 |
| 4,075,033 | A | * | 2/1978 | Knox | A47K 7/08 134/6 |
| 4,531,245 | A | * | 7/1985 | Lowd | A47K 11/00 141/337 |
| 5,463,782 | A | * | 11/1995 | Carlson | A61B 10/0038 4/661 |
| 5,941,860 | A | * | 8/1999 | Wheeler | A61F 5/451 604/327 |
| 6,158,077 | A | * | 12/2000 | Wenger | A47K 7/08 15/145 |
| 6,272,716 | B1 | * | 8/2001 | Thornton | A47K 7/08 15/150 |
| 6,689,224 | B1 | * | 2/2004 | Hillman | A47K 7/06 134/6 |
| 8,122,558 | B1 | * | 2/2012 | Gary | A47K 7/08 15/210.1 |
| 8,341,796 | B1 | * | 1/2013 | Rhee | A47K 7/08 15/210.1 |
| 8,925,137 | B1 | * | 1/2015 | Munoz | A47K 7/08 15/210.1 |

* cited by examiner

*Primary Examiner* — Erin Deery
(74) *Attorney, Agent, or Firm* — Joseph Z. Ellsworth

(57) ABSTRACT

This invention is an apparatus for allowing a person of limited means due to obesity or age or handicap, to have a bowel movement without help. This apparatus can also be used by hikers or rock climbers in national parks that need to haul out and dispose of all fecal material. The invention utilizes the movement of a paper cartridge to clean the user and collect the bowel movement.

14 Claims, 6 Drawing Sheets

PERSONAL BODY CLEANING AND STOOL COLLECTION DEVICE AND METHOD

FIELD OF THE INVENTION

This invention relates to a device for facilitating bowel movements, more specifically, a device that simultaneously collects the bowel movement and cleans the body.

BACKGROUND

People of limited mobility such as the elderly, people of size and the disabled, can find themselves requiring help during a bowel movement. This entails collecting the bowel movement and then being wiped to clean the body. Usually this would be performed by a health care professional whom is expensive and can be humiliating to endure.

SUMMARY

It is therefore, an object of the invention to provide a device that allows a person of limited means to go to the bathroom on their own and wipe themselves. An apparatus for managing a bowel movement may comprise a handle for the user to hold onto, a comfort saddle structure that fits comfortably between the legs, a loading cylinder and, a cartridge configured to fit over the loading cylinder and collect the stool and clean the body of a user.

A method for managing a bowel movement comprising: placing a cartridge on a loading cylinder, extending an extension feature through the disposal aperture, inserting the comfort saddle between a user's buttocks, and extending the cartridge to collect the bowel movement and clean the user.

A method of manufacturing a cartridge for managing a bowel movement comprising, rolling a paper sheet into a tube, folding one end of the tube shut to form an extension feature, placing the paper tube over a cartridge compressor, sliding the compression side of the cartridge compressor relative to the guide side of the cartridge compressor.

DETAILED DESCRIPTION OF THE FIGURES

Figure 1:
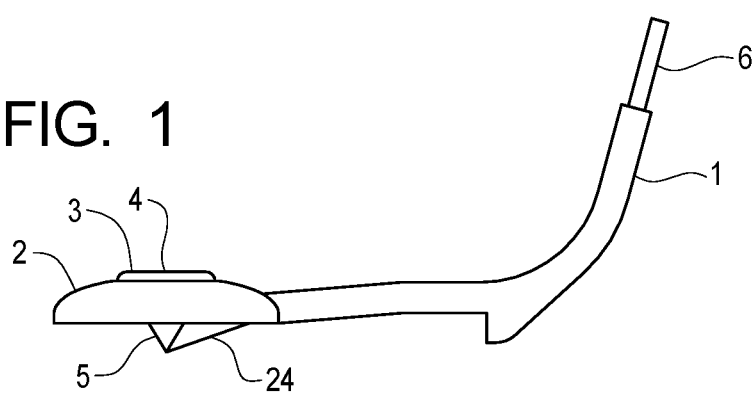

FIG. 1. Side view of the stool collection device.

Figure 1A:
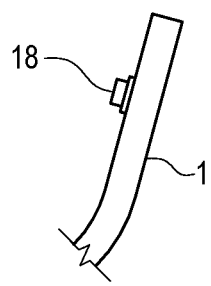

FIG. 1a. Side view cut away of stool collection device handle.

Figure 2:
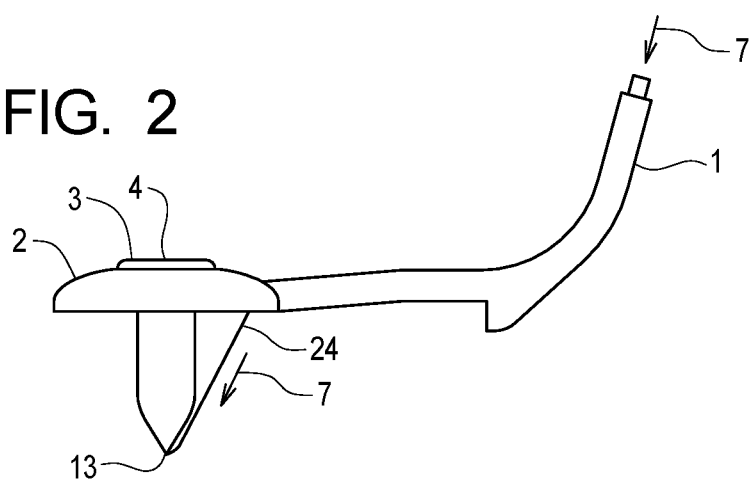

FIG. 2. Side view of the stool collection device with the extension handle depressed.

Figure 2A:
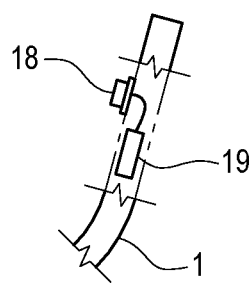

FIG. 2a. Side view cut away of the stool collection device handle showing electrical motor for extending the extension feature.

Figure 3:
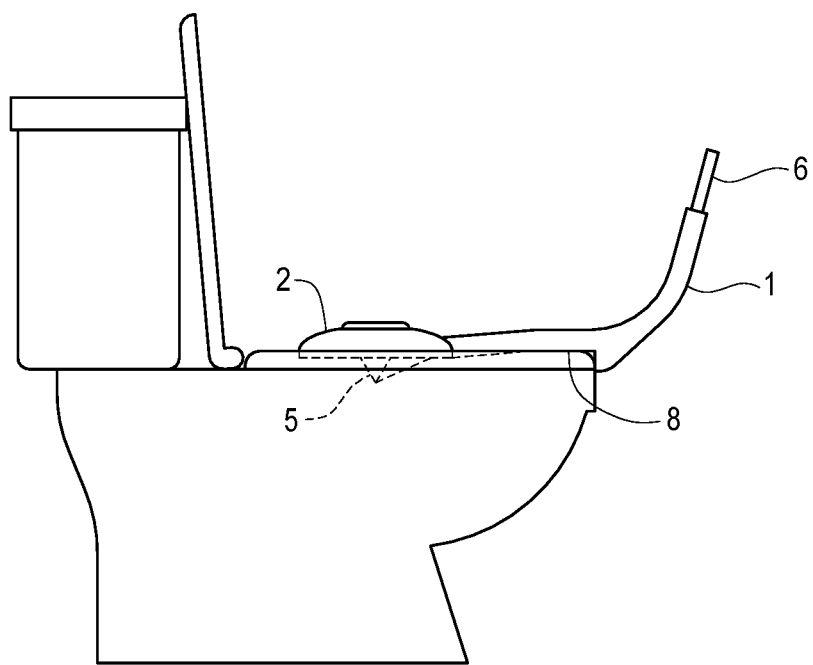

FIG. 3. Side view of stool collection device resting on a toilet.

Figure 4:
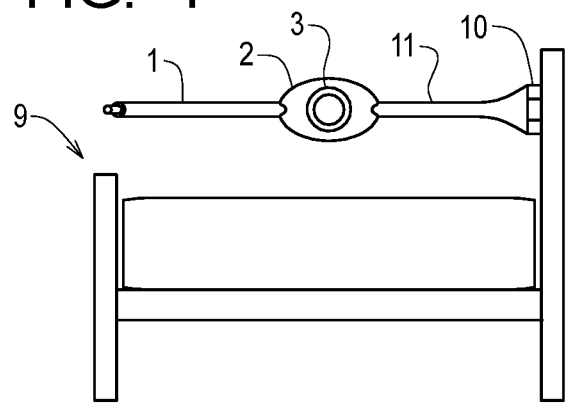

FIG. 4. End view of a bed with a stool collection device mounted to the side board.

Figure 5:
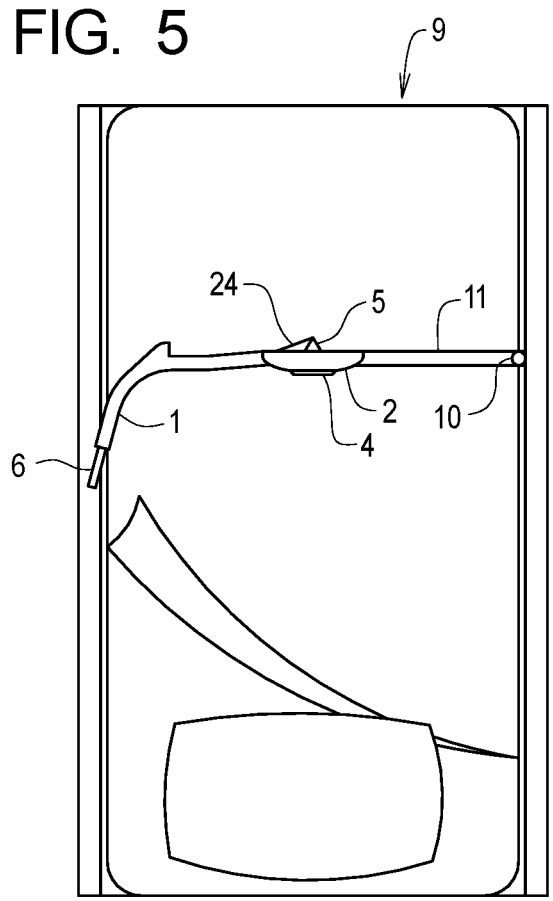

FIG. 5. Top view of a bed with a stool collection device mounted to the side board.

Figure 6:
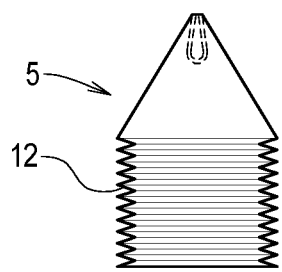

FIG. 6. Side view of a cartridge with an extension feature shown in dashes.

Figure 7:
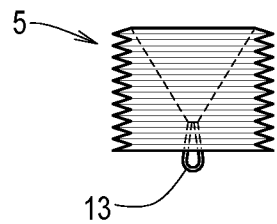

FIG. 7. Side view of a cartridge with the extension feature protruding from the bottom.

Figure 8:
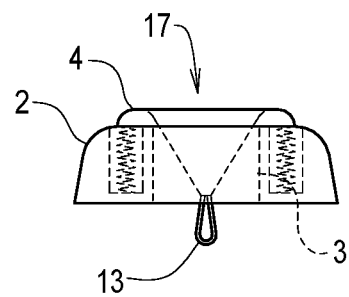

FIG. 8. Side view of a cartridge installed on a loading cylinder.

Figure 9:
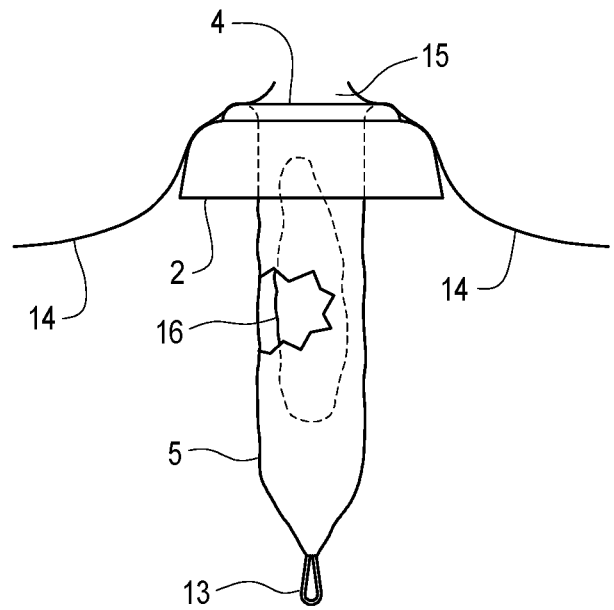

FIG. 9. End view of the stool collection device inserted between the buttocks of a person.

Figure 10:
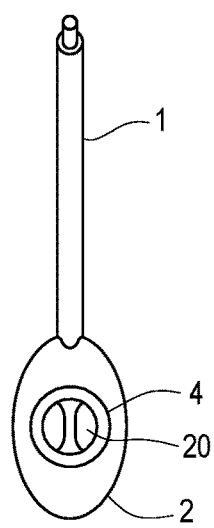

FIG. 10. Top view of the stool collection device having wiping leaves.

Figure 11:
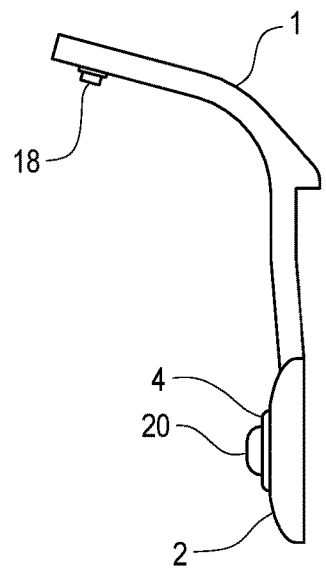

FIG. 11. Side view of the stool collection device having wiping leaves.

Figure 12:
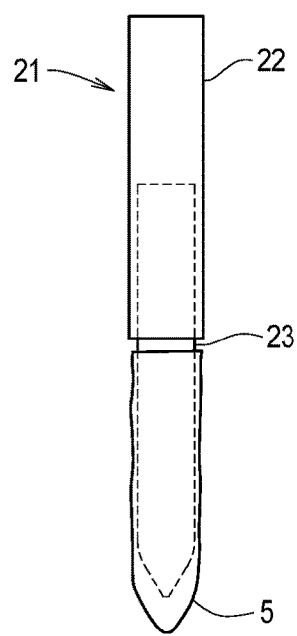

FIG. 12. Side view of a cartridge being manufactured on a cartridge compressor.

Figure 13:
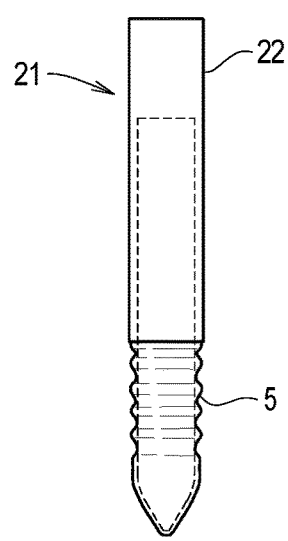

FIG. 13. Side view of a cartridge being compressed.

Figure 14:
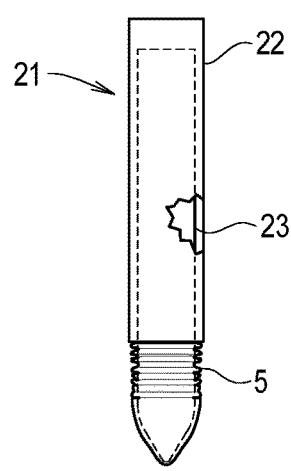

FIG. 14. Side view of a cartridge fully compressed with a compression slide.

Figure 15:
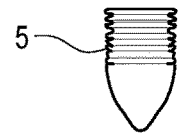

FIG. 15. Side view of a full compressed cartridge.

Figure 16:
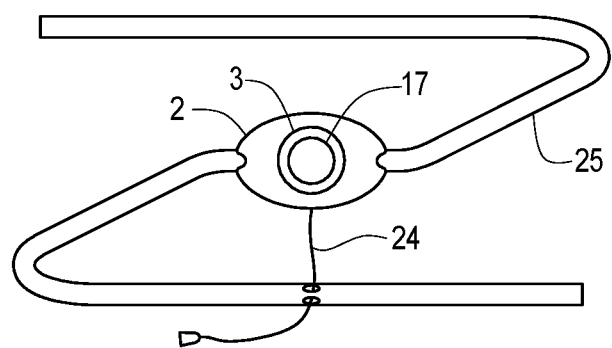

FIG. 16. Top view of a stool collection device stand.

Figure 17:
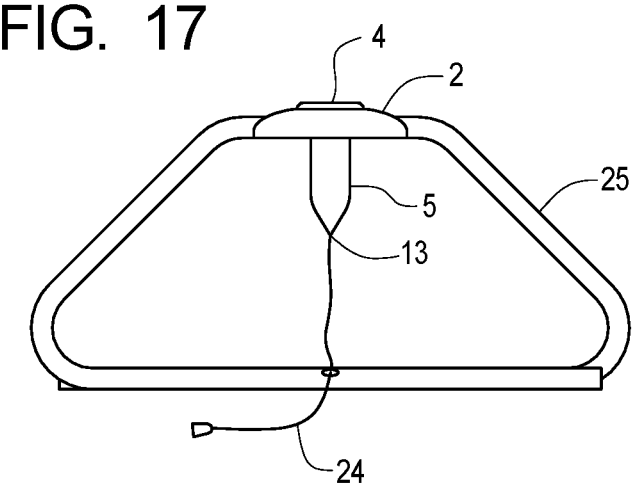

FIG. 17. Side view of a stool collection device stand.

Figure 18:
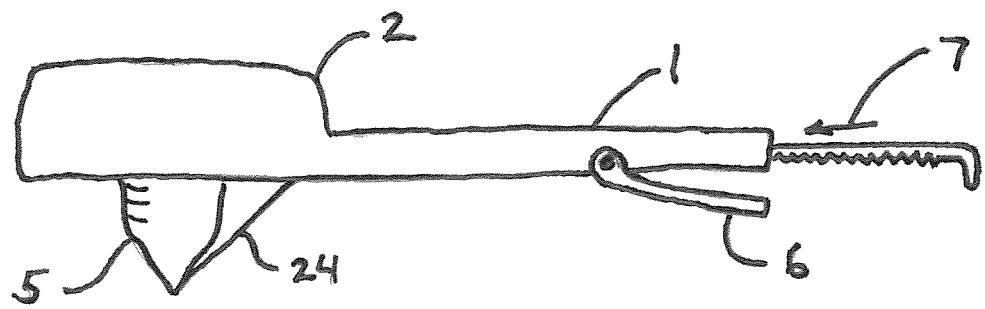

FIG. 18. Side view of a stool collection device before the cartridge is extended.

Figure 19:
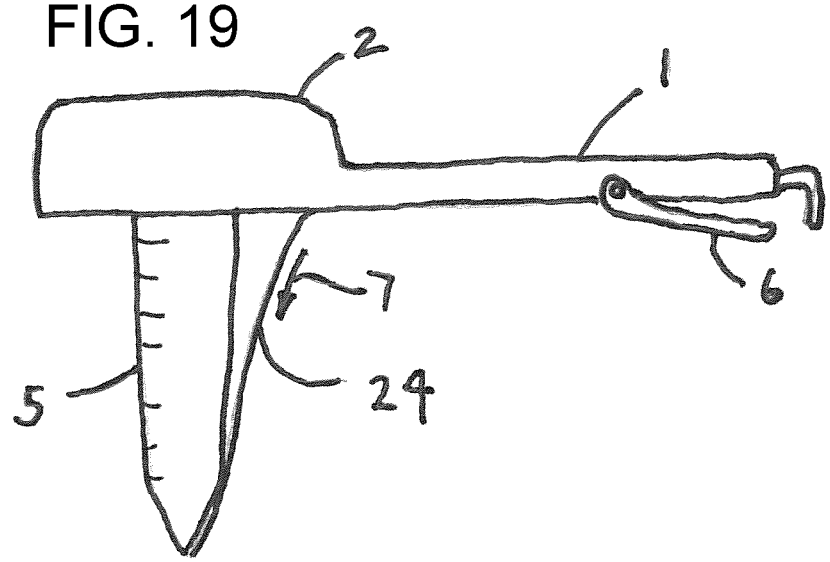

FIG. 19. Side view of a stool collection device after the cartridge is extended.

DETAILED DESCRIPTION

Many people of limited physical means due to handicap, obesity or old age have trouble using the restroom. Described below is a means for cleanly and self-sufficiently having a bowel movement within or without a restroom. Further described is a means for cleaning the excretory opening during and after a bowel movement.

As described in FIG. 1, a body cleaning and stool collecting device may have a handle 1 attached to a comfortable saddle structure 2. Centered in the saddle structure is a loading cylinder 3. The end of the loading cylinder 3 becomes a cleaning surface 4 after a cartridge 5 is loaded onto the loading cylinder 3. On the end of the handle 1 is an extension handle 6 that when pushed in the extension direction 7, will elongate the cartridge 5. The extension handle 1 is configured to pull out the cartridge 5 as a user is having a bowel movement. The motion of the cartridge 5 over the cleaning surface 4 cleans the users excretory opening 15.

As shown in FIG. 2, the extension handle 6 is depressed in the extension handle depression direction 7 which extends the extension apparatus 24. The extension apparatus may be a thin tube using compression force or line using tension force and urges an extension feature 13 and extends the cartridge 5. A typical cartridge 5 is about 10-16 inches long and the extension apparatus 24 will extend an amount similar in length to the cartridge length.

FIGS. 1a and 2a show the handle having an actuation button 18 to automatically extend the cartridge 5. The actuation button 18 sends power to an electrical motor 19 which powers the extension apparatus 24 as it elongates.

FIG. 3 shows use of the invention on a toilet, the handle 1 has a toilet land 8 that provides a pivot point to push the comfort saddle structure 2 into place under a person seated on the toilet. This may be necessary if the user was unable to reach to wipe and needed to clean the excretory opening.

For limited mobility persons on a bed 9, the invention can be attached to the side of the bed 9 for easy use and storage out of the way. In FIGS. 4 and 5, the invention is attached to a bed extender 11 that pivots about a hinge 10. I person laying on the bed 9 on their side can extend the comfort saddle 2 between their legs and hold onto the handle 1 and work the device. The user may depress the extension handle 6 as they defecate to catch the bowel movement and clean the excretory opening.

A very important part of the device is the cartridge 5 that fits over the loading cylinder 3. FIG. 6 shows the cartridge is gathered material 12 similar to paper towel. The material is tough and absorbent and can be disposed of easily. The material can be coated with a water resistant material to prevent messes. The material for the cartridge can have various usability times. As an example, the cartridge can have a usability time of 5-10 minutes because the material is very biodegradable and absorbs moisture. Another example is a cartridge material coated with wax or a polymer for one hour usability time for liquid bowel movements. The gathered material 12 is folded at the top to form an extension feature 13. The extension feature 13 is then poked back down through the gathered material 12 of the cartridge 5.

FIG. 7 shows, the tip of the cartridge has an extension loop or an extension feature 13 on the inside of the cylinder 5. In FIG. 8, this extension feature 13 extends through cartridge 5 when the cartridge 5 is loaded over the loading cylinder 3 and pulled through the disposal aperture 17 of the comfort saddle 2. The cartridge 5 is configured to extend through disposal aperture 17 and clean the user as the cartridge material 12 moves over the cleaning surface 4.

FIG. 9 shows the invention in use and inserted between the buttocks 14 and against the excretory opening (anus) 15. The cartridge 5 is extended as fecal material 16 moves through the disposal aperture 17 and into the cartridge 5. While the cartridge 5 extends, the material 12 moving over the cleaning surface 4 rubs against the anus taking any debris with it. The shape and size of the comfort saddle 2 prevents fecal material from touching the buttocks 14. The part of the body, typically the excretory opening 15, in contact with fecal material 16 is cleansed by the movement of the cartridge 5. This way the device both cleans the body and collects the bowel movement. The cartridge 5 may also be medicated. For example, the cartridge 5 can be treated with Preparation-H, to clean and medicate the anus.

The stool collection device may be electrically activated. An activation button 18 is installed on the handle 1 that activates an electrical motor 19 that drives the extension line 24 to extend the cartridge 5 as it is used.

As shown in FIGS. 10 and 11, the stool collection device may have a cleaning surface 4 enhancement by having two wiping leaves 20 that are flexible leaves that point generally upward and apply pressure to the cartridge 5 configured to contact the center of the anus and clean as the cartridge 5 is pulled through the disposal aperture 17. The wiping leaves 20 are flexible and bend away when urged by the fecal matter as it enters the disposal aperture 17 and cartridge 5.

FIGS. 12 through 15 show an example cartridge compressor 21 that compresses the cartridges 5 to form the gathered material 12. The cartridge compressor 21 has a guiding side 23 and compressing side 22. The uncompressed cartridge is slid over the guiding side 23 and held in place. The compressing side 22 is then slid down over the guiding side 23 and the cartridge is compressed to form the gathered material 12.

FIGS. 16 and 17 show a stool collection device that is incorporated into a stand 25. The stand 25 allows the comfort saddle 2 to be free standing. The free standing comfort saddle 2 allows a user to squat or sit over the device and have a bowel movement. A cartridge 5 is installed over the loading cylinder 3 and the extension feature 13 is pushed through the disposal aperture 17. The user aligns the disposal aperture 17 with the user's excretory orifice and extend the cartridge 5 with an extension apparatus 25 as the fecal material 16 is inserted. An example extension apparatus 24 may be a chord passing through the stand 25 configured to extend the cartridge 5 when pulled.

FIGS. 18 and 19 show an optional embodiment of the stool collection device. The handle 1 extends strait away from the comfort saddle 2. In this example embodiment the extension handle 6 rotates about a pivot point to ratchet the extension apparatus 24 in the extension handle depression direction 7. The extension apparatus 24 is stiff in compression and has teeth that couple to the ratchet part of extension handle 6. Repeated squeezes on the extension handle 6 moves the extension apparatus 24 in the extension handle depression direction 7. The translation of extension apparatus 24 extends the cartridge 5 to wipe the user and collect the bowel movement.

Further, the invention may comprise: an apparatus for managing a bowel movement comprising, a handle 1, a comfort saddle structure 2, a loading cylinder 3 and, a cartridge 5 configured to collect the stool 16 and clean the body of a user. The cartridge 5 may be a hollow tube with a closure 13 at one end. In one example, the cartridge is 5 a tubular paper structure open at one end and sealed closed at an opposite end. The closed end of the cartridge may be an extension feature 13 coupled to an extension apparatus 24. In one example, the extension apparatus 24 is driven by an extension handle 6 pushed in an extension direction 7.

The apparatus for managing a bowel movement may further comprise a toilet land 8 on the handle 1 configured to provide a pivot point to urge the comfort saddle structure 2 into place under a person seated on the toilet.

The apparatus for managing a bowel movement may further comprise a bed extender 11 configured to pivot about a hinge 10 in the side of a bed. The comfort saddle 2 can be rotated into position for a bowel movement in bed preferably when a user is lying on their side. In one example, the cartridge 5 is made from a paper material gathered in multiple pleats 12, having an extension feature 13 at one end. The cartridge 5 is placed over the loading cylinder 3 and the extension feature 13 is pushed over the cleaning surface 4 and through the disposal aperture 17. The cartridge 5 is configured to extend over the cleaning surface 4 and through the disposal aperture 17 as the extension feature 13 is urged away from the comfort saddle 2.

In one example embodiment the cleaning surface 4 has two wiping leaves 20 that are flexible and point generally upward and apply upward pressure to the cartridge 5 to facilitate cleaning a user. These leaves 20 may get closer to the anus and clean more skin area.

A method for managing a bowel movement comprises the following steps, placing a cartridge 5 on a loading cylinder 3, extending an extension feature 13 through the disposal aperture 17, inserting the comfort saddle 2 between a user's buttocks 14, and extending the cartridge 5 to collect the bowel movement 16 and clean the user. Further, the method may comprise attaching the extension feature 13 to the extension apparatus 24 and depressing an extension handle 6 to move the extension feature 13 in an extension handle depression direction 7. Extending the cartridge 5 pulls a portion of the cartridge 5 over a cleaning surface 4 and through the disposal aperture 17, wherein the movement of the cartridge 5 over the cleaning surface 4 is configured to clean the user and prevents further soiling of the user. In one example method, pulling the extension feature 13 extends the cartridge 5. In another example method the comfort saddle is integrated into a stand 25 which further comprises the step of sitting on the comfort saddle 2 prior to inserting the comfort saddle 2 between the buttocks 14. The cartridge 5 may be medicated to apply medicine to a user's excretory opening 15 as the cartridge 5 is extended. Example medications are witch hazel and/or other hemorrhoid treatments.

A method of manufacturing a cartridge 5 for managing a bowel movement comprises; rolling a paper sheet into a tube and bonding the sides to form the tube, then folding one end of the tube shut to form an extension feature 13 and to close out the tube to hold the fecal material 16, then placing the paper tube over a cartridge compressor 21 and, sliding the compression side 22 of the cartridge compressor 21 relative to the guide side 23 of the cartridge compressor 21. The resulting cartridge 5 has gathered pleats 12 of paper or fabric material. The cartridge is compressed from 16 inches to one inch. The cartridge 5 is open at one end and closed at the opposite end.

The invention claimed is:

1. An apparatus for managing a bowel movement comprising,
a handle,
a saddle structure,
a loading cylinder and,
a cartridge configured to collect stool and clean a body of a user,
wherein the saddle structure is configured to be inserted between a buttocks and against an anus of the user,
wherein the cartridge is extended as stool moves through the loading cylinder and into the cartridge:
wherein,
the cartridge is a hollow tube with a closure at a first end
wherein, as the cartridge extends to receive stool, the cartridge moves up over a cleaning surface and rubs against the anus removing uncollected stool.

2. The apparatus of claim 1 wherein,
the cartridge is a paper structure open at one end opposite the first end.

3. The apparatus of claim 1 wherein,
the first end of the cartridge is an extension feature and is coupled to an extension apparatus.

4. The apparatus of claim 3 further comprising,
wherein the extension apparatus is driven by an extension handle pushed in an extension direction.

5. The apparatus of claim 1 further comprising,
a toilet land configured to provide a pivot point to push the saddle structure into place under the user seated on a toilet.

6. The apparatus of claim 1 wherein,
the cartridge is made from a paper material gathered in multiple pleats, having
an extension feature at one end.

7. The apparatus of claim 1 further comprising,
a disposal aperture,
and the cleaning surface is adjacent the disposal aperture, wherein
the cartridge is placed over the loading cylinder and an extension feature is pushed through the disposal aperture.

8. The apparatus of claim 7 wherein,
the cartridge is configured to extend over the cleaning surface through the disposal aperture as the extension feature is urged away from the saddle.

9. The apparatus of claim 1 wherein,
the cleaning surface further comprises two wiping leaves that are flexible leaves that point upward and apply upward pressure to the cartridge to facilitate cleaning the user.

10. A method for managing a bowl movement comprising:
placing a cartridge on a loading cylinder of a saddle, wherein the cartridge is a hollow tube with a closure at one end and is configured to extend as stool moves through the loading cylinder and into the cartridge,
extending an extension feature of the cartridge through a disposal aperture of the saddle,
inserting the saddle between a user's buttocks, and
extending the cartridge to collect stool and clean the user by depressing an extension handle of an extension apparatus, the extension handle located on a handle of the saddle and configured to move the extension feature in an extension handle depression direction, wherein
extending the cartridge pulls a portion of the cartridge up over a cleaning surface and through the disposal aperture, wherein the movement of the cartridge over the cleaning surface is configured to rub the cartridge against the anus, thereby removing uncollected stool and preventing further soiling of the user.

11. The method of claim 10 further comprising:
attaching the extension feature to the extension apparatus.

12. The method of claim 10 wherein,
pulling the extension feature extends the cartridge.

13. The method of claim 10, further comprising,
the step of sitting on the saddle prior to inserting the saddle between the user's buttocks.

14. The method of claim 10 wherein,
the cartridge is medicated to apply medicine as the cartridge is extended.

* * * * *